US005846917A

United States Patent [19]
Oumar-Mahamat et al.

[11] Patent Number: 5,846,917
[45] Date of Patent: Dec. 8, 1998

[54] PHENOLIC IMIDAZOLINE ANTIOXIDANTS

[75] Inventors: Halou Oumar-Mahamat, Plainsboro; Andrew G. Horodysky, Cherry Hill, both of N.J.

[73] Assignee: Mobil Oil Corporation, Fairfax, Va.

[21] Appl. No.: 921,500

[22] Filed: Sep. 2, 1997

Related U.S. Application Data

[63] Continuation of Ser. No. 735,374, Oct. 21, 1996, abandoned, which is a continuation of Ser. No. 416,247, Apr. 4, 1995, abandoned.

[51] Int. Cl.$^6$ .................... C10M 133/46; C10M 135/58; C07D 403/02
[52] U.S. Cl. .................. 508/283; 548/300.1; 548/313.4; 548/313.7; 548/314.4
[58] Field of Search .................... 508/283; 548/300.1, 548/313.4, 313.7, 314.4

[56] References Cited

U.S. PATENT DOCUMENTS

| | | | |
|---|---|---|---|
| 3,725,480 | 4/1973 | Traise et al. | 548/300.1 |
| 4,626,368 | 12/1986 | Cardis | 252/49.9 |
| 4,787,996 | 11/1988 | Horodysky et al. | 252/51.5 R |
| 5,288,418 | 2/1994 | Farng et al. | 252/49.9 |

*Primary Examiner*—Jerry D. Johnson
*Attorney, Agent, or Firm*—Malcolm D. Keen

[57] ABSTRACT

Phenolic imidazolines prepared via one-step condensation of hydrocarbylpolyamino-phenols and carbonyl generating species have been found to be effective antioxidants in lubricant applications. These additives are derived from a one-step reaction using low cost phenolic amines and carbonyl compounds. In addition to their antioxidant activity, they are, because of the presence of the cyclic imidazoline groups, also expected to exhibit corrosion inhibiting and metal passivating activity.

13 Claims, No Drawings

PHENOLIC IMIDAZOLINE ANTIOXIDANTS

This application is a continuation of application Ser. No. 08/735,374 filed Oct. 21, 1996, now abandoned which is a continuation of application Ser. No. 08/416,247, filed Apr. 4, 1995, now abandoned.

FIELD OF THE INVENTION

This invention is directed to lubricant additives and compositions, reaction products, and a process for making same. Specifically, it concerns phenolic imidazolidines prepared via a one-step condensation of hydrocarbylpolyaminophenols and carbonyl generating species which are effective antioxidants in lubricant applications.

BACKGROUND OF THE INVENTION

The use of hindered phenols, such as 2,6-di-tert-butylphenol and 2,6-di-tert-butyl-para-cresol, has been well known for their thermal/oxidation stabilizing properties in a variety of lubricant, polymer and elastomer applications.

Amines have been used in the lubricants and detergent industry for their alkalinity, surface activity, and neutralization capability. Amine phosphates are one class of additives used extensively in industrial oils. Polyamine-derived succinimides are key components in ashless dispersants of engine oils. The use of amine derivatives, such as amine phosphate salts, has been widespread for several decades as corrosion inhibitors and antiwear/EP additives.

Benzotriazole or a substituted benzotriazole compound reacted with an alkyl aldehyde and dialkylhydrogen phosphites provide products which improve the load-carrying, antiwear properties of lubricant oils and greases. These reactants are disclosed in U.S. Pat. No. 4,626,368 which issued to Cardis on Dec. 2, 1986. Amine coupled condensation products of hindered phenols and phosphites are disclosed in U.S. Pat. No. 5,288,418 which issued to Farng et al. on Feb. 22, 1994. These products were found to be effective antioxidant/antiwear additives for lubricants. These patents are incorporated by reference herein.

It has now been found that combinations of an additive reaction product of a hydrocarbylpolyaminophenol and an aldehyde or carbonyl generating species provide excellent antioxidant properties in lubricant formulations.

SUMMARY OF THE INVENTION

Lubricant and fuel compositions containing a small additive concentration of a novel reaction product of a hydrocarbylpolyaminophenol and an aldehyde or carbonyl generating species provide excellent antioxidant properties in lubricant formulations. Activity of these compounds is enhanced by internal synergism between the phenolic moiety and the imidazoline formed by the reaction of two amino groups with the carbonyl moiety. Due to the presence of nitrogens, the imidazolidine group may also contribute additional detergency, metal passivating, dispersancy, high temperature stabilizing and corrosion inhibition properties to the resultant novel additives.

Products and compositions containing these novel additives show good stability and compatibility when used in the presence of other commonly used additives in lubricant compositions. In addition to conventional lubricant applications, resultant novel compounds of this invention may be used in vegetable oils and EAL (environmental awareness lubricants) to impart similar performance qualities. These novel additives are expected to provide oxidation stability, cleanliness, and detergency qualities when used in hydrocarbon, alcoholic, or mixed hydrocarbon/oxygenated fuels.

It is therefore an object of this invention to provide for a novel antioxidative phenolic imidazolidine additive and a facile process for making same.

It is another object of this invention to provide for novel phenolic imidazoline additives which exhibit exceptional oxidation protection when used in lubricants thereby outperforming the antioxidant activity of commercial hindered phenol and aromatic amine antioxidants.

It is a further object of this invention to provide for a novel antioxidative phenolic imidazolidine additive which imparts additional cleanliness, high temperature stability, antifatigue, extreme pressure, load-carrying antiwear, friction reducing, metal deactivation and corrosion inhibition characteristics to lubricants containing same.

BRIEF DESCRIPTION OF THE PREFERRED EMBODIMENTS

In the practice of this invention aliphatic or aromatic aldehydes or mixtures of both were reacted with polyaminophenols in a one step reaction to yield phenolic imidazolidine derivatives as generally described below:

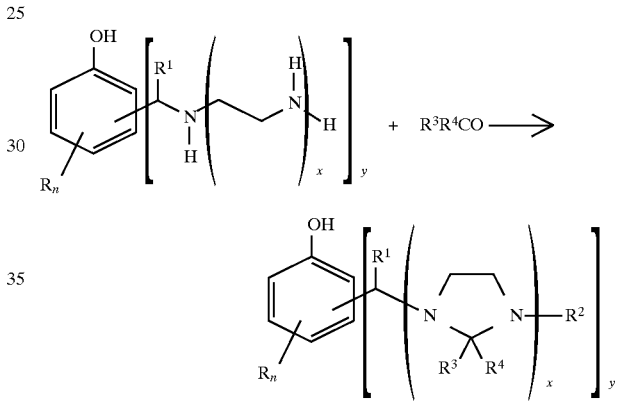

where n is 1 or 2; x is 1, 2, 3 or 4; y is 1 or 2; R is hydrogen, $C_1$ to $C_{60}$ hydrocarbyl alkyl or a $C_2$ to $C_{60}$ hydrocarbyl alkenyl which optionally contains one or more members selected from the group consisting of aryl, arylalkyl, alkylaryl, sulfur, oxygen or nitrogen; $R^1$ is hydrogen, $C_1$ to $C_{60}$ hydrocarbyl alkyl which optionally contains a member selected from the group consisting of sulfur, oxygen or nitrogen; $R^2$ is hydrogen when x=1 or 3 or is an ethylene imine group when x=2 or 4; $R^3$ and $R^4$ are hydrogen, $C_1$ to $C_{60}$ hydrocarbyl alkyl which optionally contains a member selected from the group consisting of sulfur, oxygen, or nitrogen. The hydrocarbyl in R is preferably an alkenyl or an alkyl containing the appropriate number of carbon atoms. In $R^1$, $R^3$, and $R^4$, hydrocarbyl is preferentially an alkyl.

Stoichiometry of the reaction is dictated by the number of ethyleneamino groups present in the alkylated polyaminophenols. One or a mixture of several aldehydes, or carbonyl generating species, or aldehydes and carbonyl generating species can be used. An excess of one reactant or another is desirable, on occasion. Temperatures between 100° C. and 160° C. are preferred. The preferred reaction time is about 3 to about 24 hours.

In accordance with the equation above expressed, the reactants may be simultaneously reacted, i.e., the hydrocarbylpolyaminophenol, and the aldehyde or carbonyl generating species may be reacted in a one-step batch or one step continuous process.

Generally speaking, conditions for the above described reactions may vary widely depending upon specific reactants, the presence or absence of a solvent and the like. Any suitable set of reaction conditions known to the art may be used. Generally, stoichiometric quantities of reactants are used. However, equimolar, more than equimolar or less than equimolar amounts may be used. An excess of up to 100% or more of any of the reactants can be used. Preferably, the molar ratio of reactants varies from about 0.1:5 moles to about 0.5:1 moles respectively of amine to aldehyde or a carbonyl generating species. The reaction temperature may vary from ambient to about 250° C. or reflux, the pressure may vary from ambient or autogenous to about 500 psi.

The additives embodied herein are utilized in lubricating oil or grease compositions in an amount which imparts significant antiwear characteristics to the oil or grease as well as reducing the friction of engines operating with the oil in its crankcase. Concentrations of about 0.001 to about 10 wt % based on the total weight of the composition can be used. Preferably, the concentration is from 0.1 to about 3 wt. %.

Suitable amines include but are not limited to the following: diethylenetriamine, triethylenetetramine tetraethylenepentamine, polyoxyalkylenediamines ("JEFFAMINE D" series, ED series), polyoxyalkylenetriamines ("JEFFAMINE T-series"), N-alkyl-1,3-diaminopropane, alkylated phenolic polyamines etc. or mixtures of such amines. A preferred amine comprises an alkylated phenolic polyamine. These preferred amines are sold as "CARDOLITE" alkylated phenolic polyamines by the Cardolite Corporation.

Suitable aliphatic or aromatic aldehydes and mixtures thereof which can be used herein include but are not limited to the following; butyraldehyde, 2-ethyhexanal, formaldehyde, para-tolualdehyde, para-ethylbenzaldehyde, salicylaldehyde, and compounds similar thereto. Paraformaldehyde is a preferred carbonyl generating species. Of these, para-tolualdehyde, para-ethylbenzaldehyde, and salicylaldehyde are preferred.

Any suitable hydrocarbon solvent such as toluene, hexane or a xylene may be used if desired.

The additives have the ability to improve the above noted characteristics of various oleaginous materials such as hydrocarbyl lubricating media which may comprise liquid oils in the form of either a mineral oil or a synthetic oil, or in the form of a grease in which the aforementioned oils are employed as a vehicle.

In general, mineral oils, both paraffinic, naphthenic and mixtures thereof, employed as the lubricant, or grease vehicle, may be of any suitable lubricating viscosity range, as for example, from about 45 SUS at 100° F. to about 6,000 SUS at 100° F. and preferably, from about 50 to about 250 SUS at 210° F. These oils may have viscosity indexes preferably ranging to about 95. The average molecular weights of these oils may range from about 250 to about 800. Where the lubricant is to be employed in the form of a grease, the lubricating oil is generally employed in an amount sufficient to balance the total grease composition, after accounting for the desired quantity of the thickening agent, and other additive components to be included in the grease formulation.

A wide variety of materials may be employed as thickening or gelling agents. These may include any of the conventional metal salts or soaps, which are dispersed in the lubricating vehicle in grease-forming quantities in an amount sufficient to impart to the resulting grease composition the desired consistency. Other thickening agents that may be employed in the grease formulation may comprise the non-soap thickeners, such as surface-modified clays and silicas, aryl ureas, calcium complexes and similar materials. In general, grease thickeners may be employed which do not melt and dissolve when used at the required temperature within a particular environment; however, in all other respects, any material which is normally employed for thickening or gelling hydrocarbon fluids for forming grease can be used in preparing grease in accordance with the present invention.

In instances where synthetic oils, or synthetic oils employed as the lubricant or vehicle for the grease, are desired in preference to mineral oils, or in combination therewith, various compounds of this type may be successfully utilized. Typical synthetic oils include, but are not limited to, polyisobutylene, polybutenes, hydrogenated polydecenes, polypropylene glycol, polyethylene glycol, trimethylpropane esters, neopentyl and pentaerythritol esters, di(2-ethylhexyl) sebacate, di(2-ethylhexyl) adipate, dibutyl phthalate, fluorocarbons, silicate esters, silanes, esters of phosphorus-containing acids, liquid ureas, ferrocene derivatives, hydrogenated synthetic oils, chain-type polyphenyls, siloxanes and silicones (polysiloxanes), alkyl-substituted diphenyl ethers typified by a butyl-substituted bis(p-phenoxy phenyl) ether, and phenoxy phenylethers.

It is to be understood, however, that the compositions contemplated herein can also contain other materials. For example, corrosion inhibitors, extreme pressure agents, low temperature properties modifiers and the like can be used as exemplified respectively by metallic phenates or sulfonates, polymeric succinimides, non-metallic or metallic phosphorodithioates and the like. These materials do not detract from the value of the compositions of this invention, rather the materials serve to impart their customary properties to the particular compositions in which they are incorporated.

The additives in accordance with the invention are believed to be highly useful in fuel compositions, particularly in liquid hydrocarbon fuels or oxygenated fuels such as alcoholic or ether-containing fuels and the like and mixtures thereof. The present additives are used in fuel compositions in amounts ranging from about 1 to about 1,000 pounds of additive per 1,000 barrels of fuel and preferably from about 10 to about 250 pounds per 1,000 pounds of fuel. In addition to liquid hydrocarbon and oxygenated combustion fuels, distillate fuels and fuel oils are also contemplated.

The following examples are merely illustrative and are not meant to be limitations.

EXAMPLE 1

Approximately 230 grams (0.5 mol) of an alkylated phenolic polyamine ("CARDOLITE NX4503," commercially obtained from Cardolite Corporation) and about 120 grams (1 mol) of para-tolualdehyde in 300 ml of toluene were heated at reflux to a temperature of about 130° C. for 5 hours under an inert atmosphere. Water formed during the reaction was constantly removed by azeotropic distillation using a moisture trap, (Dean-Stark apparatus). The solvent was then stripped by distillation by raising the temperature to 140° C. Light ends of the remaining residue were removed under vacuum to yield 324 grams of thick brown liquid.

EXAMPLE 2

The reaction was run similarly to Example 1 using about 219 grams (0.4 mol) of "CARDOLITE NX4502" in place of 0.5 mol. of "CARDOLITE NX4503" and about 107 grams (0.8 mol) of para-ethylbenzaldehyde and 49 grams (0.4 mol.) of salicylaldehyde in place of 1 mol. of para-tolualdehyde.

The antioxidant properties of the examples were evaluated using the Catalytic Oxidation Test at both 325° F. for 40 hours and 72 hours. The Catalytic Oxidation Test consists basically of bubbling a stream of air through a volume of the lubricant at the rate of five liters per hour respectively at 325° F. for 40 hours and 72 hours. See U.S. Pat. No. 3,682,980 incorporated herein by reference for further details.

The results displayed on the following two tables show exceptionally good control of oxidation as measured by change in acidity and viscosity increase. The products of the Examples were compared to high quality hindered phenol and aryl amine antioxidants and found to be significantly superior to these two types of commercial antioxidants.

TABLE 1

Catalytic Oxidation Test
40 Hours, 325° F.

| Item | Additive Conc. (wt %) | Change in Acid Number ΔTAN | Percent Change in Viscosity ΔKV% |
|---|---|---|---|
| Base oil (200 second, solvent refined, paraffinic neutral, mineral oil) | — | 13.6 | 338.9 |
| Example 1 in above base oil | 1 | −0.02 | 1.6 |
| Example 2 in above base oil | 0.5 | 1.2 | 10.9 |
| "ETHYL 702", commercial hindered phenolic antioxidant | 1 | 9.8 | 72.3 |
| "IRGANOX L57", commercial alkylated diphenylamine antioxidant | 1 | 4.3 | 24.1 |

TABLE 2

Catalytic Oxidation Test
72 Hours, 325° F.

| Item | Additive Conc. (wt %) | Change in Acid Number ΔTAN | Percent Change in Viscosity ΔKV% |
|---|---|---|---|
| Base oil (200 second, solvent refined, paraffinic neutral, mineral oil) | — | 24.1 | 2,942.6 |
| Example 1 in above base oil | 1 | −0.02 | 3.5 |
| Example 2 in above base oil | 0.5 | 1.7 | 23.6 |
| "ETHYL 702", commercial hindered phenolic antioxidant | 1 | 18.9 | 635.1 |
| "IRGANOX 157", commercial alkylated diphenylamine antioxidant | 1 | 14.7 | 121.4 |

EVALUATION OF PRODUCTS

The products of this invention exhibit very good antioxidant activities as shown above. These additives are novel and unique. They are readily made in a one step procedure. The products of this invention, when used in premium quality automotive, industrial and environmental awareness lubricants, can significantly enhance thermal and oxidation stability, the antiwear property, and extend service life.

Although the present invention has been described with preferred embodiments, it is to be understood that modifications and variations may be resorted to, without departing from the spirit and scope of this invention, as those skilled in the art will readily understand. Such variations and modifications are considered to be within the purview and scope of the appended claims.

What is claimed:

1. An improved lubricant composition comprising a major proportion of an oil of lubricating viscosity or grease prepared therefrom comprising a liquid hydrocarbon and a minor amount of a multifunctional antiwear, antioxidant, anticorrosion, metal passivating, additive product of reaction prepared by (a) reacting a alkylated phenolic ethylene polyamine with (b) an aromatic aldehyde or ketone wherein the reaction is carried out in molar ratios of reactants varying from equimolar to more than equimolar to less than equimolar at temperatures varying from ambient to about 250° C. or reflux, under pressures varying from ambient or autogenous to about 500 psi for a time sufficient to obtain a phenolic imidazolidine derived additive product of reaction.

2. The composition of claim 1 where the reactants are an alkylated phenolic ethylene polyamine, para-tolualdehyde, which are reacted at temperatures between about 100° C. to about 160° C. under ambient pressure for about 3 to about 24 hours.

3. The composition of claim 1 where the reactants are an alkylated phenolic ethylene polyamine, and salicylaldehyde which are reacted at temperatures between about 100° C. to about 160° C. under ambient pressure for about 3 to about 24 hours.

4. The composition of claim 1 where in step (a) the polyaminophenol is an alkylated phenolic ethylene polyamine and (b) the aldehyde is selected from para-tolualdehyde, para-ethylbenzaldehyde, salicylaldehyde, or mixtures thereof.

5. The composition of claim 1 wherein the lubricant contains from about 0.001 to about 10 wt % based on the total weight of the composition of the additive product of reaction.

6. A process for preparing a multifunctional antiwear, antioxidant, anticorrosion, metal passivating, additive product of reaction which is prepared by (a) reacting a alkylated phenolic ethylene polyamine with (b) an aromatic aldehyde or ketone, wherein the reaction is carried out in molar ratios of reactants varying from equimolar to more than equimolar to less than equimolar at temperatures varying from ambient to about 250° C. or reflux, under pressures varying from ambient or autogenous to about 500 psi for a time sufficient to obtain a phenolic imidazolidine derived additive product of reaction.

7. The process of claim 6 where the reactants are an alkylated phenolic ethylene polyamine and para-tolualdehyde which are reacted at temperatures between about 100° C. to about 160° C. under ambient pressure for about 3 to about 24 hours.

8. The process of claim 6 where the reactants are an alkylated phenolic ethylene polyamine and salicylaldehyde which are reacted at temperatures between about 100° C. to about 160° C. under ambient pressure for about 3 to about 24 hours.

9. The process of claim 6 wherein the aldehyde is selected from para-tolualdehyde, para-ethylbenzaldehyde, salicylaldehyde, or mixtures thereof.

10. A multifunctional antiwear, antioxidant, anticorrosion, metal passivating, additive product of reaction which is prepared by (a) reacting a alkylated phenolic ethylene polyamine with (b) an aromatic aldehyde or ketone wherein the reaction is carried out in molar ratios of reactants varying from equimolar to more than equimolar to less than equimolar at temperatures varying from ambient to about 250° C. or reflux, under pressures varying from ambient or autogenous to about 500 psi for a time sufficient to obtain a phenolic imidazolidine derived additive product of reaction.

11. The additive product of reaction in accordance with claim 10 wherein said product of reaction is prepared from an alkylated phenolic ethylene polyamine, para-tolualdehyde which are reacted at temperatures between about 100° C. to about 160° C. under ambient pressure for about 3 to about 24 hours.

12. The additive product of reaction in accordance with claim 10, wherein said product of reaction is prepared from an alkylated phenolic ethylene polyamine, para-ethylbenzaldehyde, and salicylaldehyde which are reacted at temperatures between about 100° C. to about 160° C. under ambient pressure for about 3 to about 24 hours.

13. The additive product of reaction in accordance with claim 10 wherein the aldehyde is selected from para-tolualdehyde, para-ethylbenzaldehyde, salicylaldehyde, or mixtures thereof.

* * * * *